United States Patent [19]

Hartel et al.

[11] Patent Number: 5,182,942

[45] Date of Patent: Feb. 2, 1993

[54] PROCESS AND APPARATUS FOR UTILIZATION OF FUELS WITH ALCOHOL ADDITIVES FOR AN INTERNAL COMBUSTION ENGINE

[75] Inventors: Gunter Hartel, Neuss; Armin Schurfeld, Meerbush; Karl-Heinrich Losing, Alpen; Dieter Thonnesen, Viersen; Ulrich Remde, Meerbush, all of Fed. Rep. of Germany

[73] Assignee: Pierburg GmbH, Neuss, Fed. Rep. of Germany

[21] Appl. No.: 770,997

[22] Filed: Oct. 1, 1991

[30] Foreign Application Priority Data

Oct. 1, 1990 [DE] Fed. Rep. of Germany ....... 4031008

[51] Int. Cl.$^5$ ...................... G01N 25/02; F02D 41/00
[52] U.S. Cl. .................... 73/61.46; 73/61.61; 123/1 A; 374/25
[58] Field of Search ................. 73/61.3, 61.1 R, 61.43, 73/61.46, 61.61; 252/408.1; 203/2, 3; 374/16, 25, 27; 123/1 A; 422/82.12

[56] References Cited

U.S. PATENT DOCUMENTS

| | | | |
|---|---|---|---|
| 1,658,950 | 2/1928 | Stein | 73/61.1 R |
| 3,732,723 | 5/1973 | Goolsby et al. | 374/27 X |
| 4,528,635 | 7/1985 | Juodikis et al. | 73/61.3 X |
| 4,589,277 | 5/1986 | Collins et al. | 73/61.3 X |
| 4,939,467 | 7/1990 | Nogami et al. | 73/61.1 P X |
| 4,942,848 | 7/1990 | Terasaka | 123/1 A |
| 4,945,863 | 8/1990 | Schmitz et al. | 73/61.1 R |
| 5,005,402 | 4/1991 | Pischinger et al. | 123/1 A X |

OTHER PUBLICATIONS

Brady, J. E., G. E. Humistor, "General Chemistry: Principles and Structure" NY, John Wiley & Sons, 1982, pp. 338-339.

*Primary Examiner*—Tom Noland
*Assistant Examiner*—Michael Brock
*Attorney, Agent, or Firm*—Ladas & Parry

[57] ABSTRACT

Process and apparatus for utilization of fuels with alcohol additives for an internal combustion engine in which during the heating of a sample quantity of a fuel mixture of a conventional fuel and alcohol there is a delay in the temperature increase in the region of the boiling point of the alcohol, due to its heat of vaporization. The apparatus (a) detects this temperature region, which characterizes the type of alcohol in the mixture, and (b) determines the extend of the delay in the temperature increase which characterizes the percent admixture of the alcohol in the fuel mixture. The measurement values obtained during the vaporization are utilized to produce a correction signal in a control device to effect a change in the air-fuel ratio in the fuel mixture former of the internal combustion engine.

25 Claims, 4 Drawing Sheets

PROCESS AND APPARATUS FOR UTILIZATION OF FUELS WITH ALCOHOL ADDITIVES FOR AN INTERNAL COMBUSTION ENGINE

FIELD OF THE INVENTION

The invention relates to a process and apparatus for the utilization of fuels with alcohol additives for an internal combustion engine.

BACKGROUND

In addition to high test and regular gasoline and diesel fuel, alcohols, such as methanol, ethanol, propanol, isobutanol, etc. are suitable as fuels for internal combustion engines.

The calorific value of the combustible fuel-air mixture is a determining factor for the power of the engine. For a stoichiometric mixing ratio, the calorific value of the mixture for substantially all utilizable liquid fuels and liquified petroleum gases lies between 700 and 735 Kcal/kg; they are thus almost equal and engine power losses should not be expected by mixing methanol or other alcohols into the fuel mixture. In addition, most of the other properties of alcohols are such that they can mixed with common liquid fuels without anything further and they cause no disturbances in practical engine operation.

An alcohol composition is particularly desirable for the reason that alcohols are suitable as a refining fuel for low-grade gasolines. By adding, for example, methanol to regular gasoline, the anti-knock property of the gasoline can be substantially improved so that with this mixture even high compression internal combustion engines can be operated. Therefore, it becomes unnecessary to add anti-knocking agents to the fuel, which may be harmful to the environment.

Therefore, alcohols are becoming of increasing importance in the USA for environmental reasons, particularly due to the stricter regulations in California.

In addition, alcohols, particularly methanol, can be produced from coal relatively cheaply, and alcohols will thus be available in large quantities well into the distant future. In particular, ethanol is environmental-friendly, if it is obtained from plant products. Alcohols are thus a suitable supplement for fossil fuels whose supply is ultimately limited.

However, it is disadvantageous that the specific minimum air requirement for complete combustion in the case of alcohols is less than for conventional fuels. For the same aspirated air quantity, a correspondingly higher quantity of fuel must be introduced to the engine in the case of alcohol or for a mixture of gasoline and alcohol in order to obtain a stoichiometric air-fuel ratio. This makes necessary a corresponding adjustment of the mixture-forming means, i.e. fuel injection or carburation systems of the internal combustion engine. Moreover, since the alcohols are usually added in varying amounts, as necessary, or can vary in tho vehicle fuel tank when different types of fuel are added to the tank, the required air-fuel ratio for a stoichiometric mixture must be determined anew in the electronic control device for the mixture-forming means according to the alcohol fraction in the fuel tank.

In DE-OS 40 19 188 there is disclosed a multicomponent engine control with a fuel sensor for determining the mixture fraction of methanol in a fuel-methanol mixture, whose output signal is used for subsequently establishing a stored engine fuel-control parameter. The fuel sensor is preferably a capacitive dielectric sensor, which contains two electrode plates immersed in the fuel and arranged in spaced relation from one another. The dielectric constant of the fuel is detected by measurement of the capacitance between the two electrode plates, the added fraction of methanol being derived from the dielectric constant.

This measurement system, however, has a high sensitivity to vapor lock. In addition, this fuel sensor is only suitable to detect the mixture fraction of a previously known alcohol (e.g., methanol).

A device for automatic of adaption of an internal combustion engine to the requirements of the selective use of various types of liquid fuels is known from DE-OS 22 59 323 which has a closed measurement tank for flow therethrough of fuel from an inlet to an outlet. In the measurement tank a partial quantity of fuel is vaporized under the effect of applied heat, whereby the relative size of the vapor-filled space inside the measurement tank serves as a measurement for determining the different types of fuels.

A disadvantage of this system is that it can only be established whether a specific fraction has been exceeded or fallen below, whereby even here this fraction must be known beforehand in order to arrange the measurement sensor of this device at a specific level in the measurement tank.

SUMMARY OF THE INVENTION

Proceeding from the above, an object of the invention is to provide a process and apparatus for utilization of fuels with alcohol additives for an internal combustion engine of the aforesaid type which avoid the enumerated disadvantages of the known methods and apparatus.

The invention is based on the fact that for mixtures of conventional fuels (gasoline, diesel fuel) with alcohols (methanol, ethanol, etc.) a more or less sharply expressed delay in temperature increase is exhibited based on the heat of vaporization of the admixed types of alcohol and the quantities of the alcohols when a sample with a defined performance is heated in the region of the boiling point of the alcohol. Thus, the extent of the delay of the temperature increase is dependent on the percent admixture of alcohol and the position of the temperature region in which the delay of the temperature increase is effected, depends on the type of alcohol admixture.

In order to effect the process of the invention, the invention contemplates apparatus which detects the temperature region in which the delay in temperature increase occurs, whereby the type of alcohol is defined, and which further detects the extent of the delay of temperature increase, whereby the percent admixture of this alcohol is defined. The measurement values obtained during the vaporization (temperature value and/or time) and/or a correction signal produced in a control device effects a change in the input of fuel or the input of air into the internal combustion engine to provide a determined ratio of air and fuel mixture.

With this invention it is possible to distinguish between various alcohols and their concentration in the fuel,, in which, for example, after each engine start, a measurement is conducted and the results of the measurements are utilized to control the air-fuel mixture supplied to the internal combustion engine according to the admixed type of alcohol.

Advantageously, the linear relationship between the delay times in relation to the alcohol concentration and the substantial independence of the boiling course of gasoline due to the utilization of the heat of vaporization of the alcohol offers a good basis for high measurement accuracy.

Possible water fractions present in the fuel are of negligibly small influence due to their small specific heat in comparison to the heat of vaporization of the alcohol.

A further advantage of the method of the invention is its insensitivity to vapor lock.

DETAILED DESCRIPTION OF PREFERRED EMBODIMENTS

Figure 1:
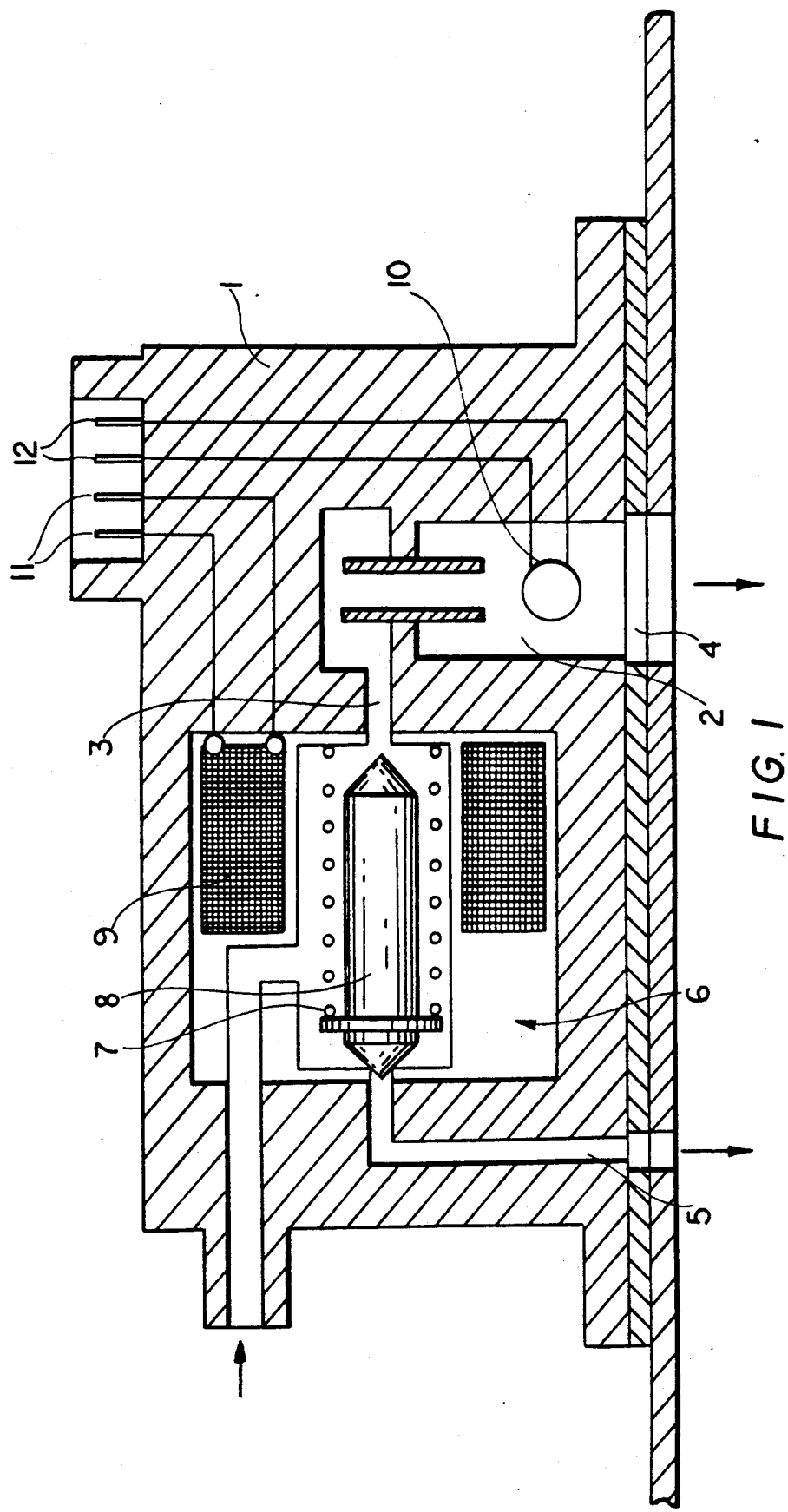
FIG. 1 is a sectional view through a vaporization device according to one embodiment of the invention.

FIG. 1 shows a device for vaporizing a sample quantity of fuel comprising a housing 1 with a vaporization chamber 2 having respective inlet and outlet channels 3, 4. The housing has a return or bypass channel 5, and the inlet channel 3 and return channel 5 are selectively opened and closed by a valve means 6 having a spring 7 acting on a valve body 8 and a magnetic coil 9 also acting on the valve body to overcome the force of the spring. A heating element 10 in the form of a positive temperature coefficient heating element or PTC is arranged in the vaporization chamber 2 and element 10 also serves as a temperature measurement means site and a sampling site. The magnetic coil 9 and the heating element 10 are controlled by a control device (not shown) by means of control leads 11, 12.

METHOD OF THE INVENTION

If the device for vaporizing- a sample quantity of fuel is in the initial or rest position, valve body 8 closes return channel 5 under the force of spring 7 and the fuel continuously flows to the vaporization chamber 2 through the opened inlet channel 3 and wets heating element 10 and then flows through outlet channel 4 back to the fuel tank.

Before the beginning of a measurement cycle, valve body 8 closes inlet channel 3 by activation of the magnetic coil 9 through a signal carried by control leads from the control device, and opens return channel 5, so that fuel no longer reaches vaporization chamber 2, which thereby is emptied of fuel through outlet channel 4 except for heating element 10 which is still wet.

According to a process step 1, by applying a voltage to heating element 10, the sample quantity of fuel in heating element 10 is heated which produces vaporization of the alcohol fraction in the fuel.

Figure 2:
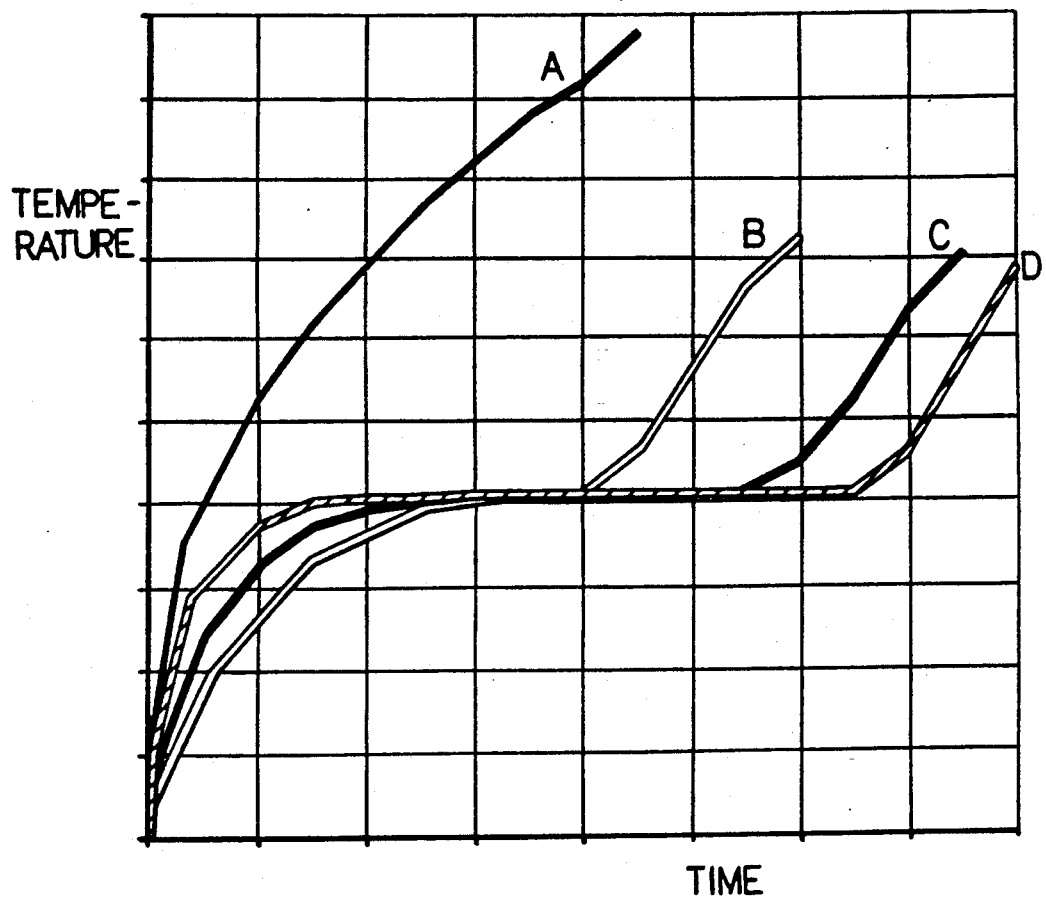
FIG. 2 is a graph illustrating the relation of temperature with respect to time of a heated methanol-fuel mixture.

FIG. 2 shows the time-temperature relation (T =f(t)) of a fuel-methanol mixture, in which curve A corresponds to a 0% fraction of methanol (standard fuel) and curves B-D correspond to a 50-100% fraction of methanol. A delay or interruption in the increase in temperature is clearly evident for each of curves B, C, D approximately at the temperature level of the boiling point of methanol (approximately 65° C.).

According &o a process step 2, the fuel sample temperature is continuously measured—in this embodiment, indirectly from PTC 10 by measurement of the current intensity, since the resistance is changed with heating, whereby the current flow is reciprocally varied during constant voltage—and the temperature gradient of the sample quantity of fuel is determined by producing the differential dT/dt of heating curve T=f(t).

In a third process step, with an established difference, i.e., for a specific percent difference between the temperature gradient determined and that of a prespecified temperature gradient of a standard fuel, the fuel sample temperature is measured and a vaporization time measurement is begun, in which the heating is maintained constant from this start of vaporization time measurement. Up until the beg vaporization time measurement, the fuel sample quantity may be heated with variable or constant voltage.

In a fourth process step, in the case of establishing a temperature gradient of the actual sample which is comparable to the initial temperature gradient of the standard fuel, the sample temperature is measured, the vaporization time measurement is stopped, and the total vaporization time is established.

Process steps 3 and 4 are explained in more detail on the basis of FIG. 2. If, for example, a 50% alcohol admixture is present (curve B), then the time measurement is begun when curve B changes from its first steep slope to its flat path (detection of the alcohol type of temperature level) and when curve B again changes to a steep slope after a specific vaporization time, the time measurement is stopped, whereby the total time between start and stop of the time measurement provides information on the percent fraction of type type of alcohol. In this regard, the value of temperature at which temperature increase is interrupted determines the type of alcohol present in the fuel mixture whereas the length of time of the temperature interruption determines the concentration of the alcohol in the mixture.

In a fifth process step, a correction signal is formed from the determined temperature and time of vaporization values by comparison with reference values stored in a performance characteristic storage unit of the control device or performance characterisitics specific to the alcohol type which signal may be utilized in a sixth process step, if necessary, for modifying the engine control variables, for example, the introduction of additional fuel or air to the mixture forming means.

The correction signal is stored in a seventh process step until it is confirmed or made current by a new fuel sample measurement.

According to the fifth process step, the measurement cycle of the vaporization device is terminated, the current supply to magnetic coil 9 and to heating element 10 is halted, valve body 8 is returned to its rest position by the force of spring 7, whereby return channel 5 is closed and inlet channel 3 is opened, and the vaporization chamber is subject to a flow-through of fresh fuel, and is flushed and cooled.

In a modification in the second process step, the temperature increase of the sample quantity of fuel is monitored until a first temperature threshold is reached below the boiling region of an alcohol;

in the third process step, when the first temperature threshold is exceeded, the vaporization time measurement is begun and this proceeds along a reproducible heating capacity course, and the temperature increase is monitored in the fourth process step until a second temperature threshold is reached above the boiling region of the alcohol, and then the vaporization time measurement is stopped, and the total vaporization time is established. The fifth, sixth and seventh process steps take place as already described above.

It is also conceivable to provide another temperature threshold, whereby, for example, a first temperature threshold lies below the boiling region of methanol, a second temperature threshold lies between the boiling regions of methanol and ethanol, and a third temperature threshold lies above the boiling region of ethanol.

When the first temperature threshold is exceeded, a first vaporization time measurement is begun, which is stopped when the second temperature threshold is exceeded (then detection of methanol is possible due to the temperature level, and establishment of the percent fraction of methanol is possible based on the length of vaporization time), or which is stopped after exceeding the third temperature threshold after a relatively short period of time (detection of standard fuel based on the temperature level).

In the device described according to FIG. 1, the temperature measurement can also be conducted by a separate temperature sensor, which is arranged as close as possible to the heating element or in actual contact therewith, so that a good heat flow is present. In addition, the valve means can be arranged and designed, for example, such that only the inlet channel to the vaporization chamber is opened or closed, as necessary.

Increasingly stricter exhaust regulations make it necessary that even small and very small working time frames of an internal combustion engine (e.g., cold start, idling, hot start, and so forth) must be subjected to an ever increasing optimization of exhaust emissions. For this reason, the previously described process is further improved as follows.

When the internal combustion engine is started (cold or hot start), a measurement cycle is immediately initiated for formation of the correction signal, but a new correction signal is available only after a specific time, which is necessary in order to conduct process step 1 to 7.

For starting and up to the establishment of a new correction signal, the last stored correction signal is used.

After starting, generally several measurements are conducted in sequence until the measurement value has stabilized.

In this way the mixture of fuel instantaneously supplied, for example, to the injector the injection valves is detected, in the course of fuel return to the fuel tank if the measurement device is arranged in the return line to the tank, as is preferable.

However, it is also conceivable to correct the last stored correction signal as a function of the filling state of the fuel tank or to override it until a new correction signal is present from the vaporization device.

In this way, in addition to the stored correction signal, upon stopping the internal combustion engine, the filling state of the fuel tank is also detected and stored, and upon starting, this is compared with the actual filling state of the tank. It still must be determined if the amount of fuel added during filling is significant. This can be affected by measuring fill time. If the actual filling state is detected only after the presence of the new correction signal (slow tank filling indication), the following process course A is proposed, while for a rapid tank filling indication, thus with the presence of the actual filling state before establishing the new correction signal, a process course B is specified.

PROCESS COURSE A slow tank filling indication

Starting is conducted with the us ®of the last stored correction signal, while at the same time the tank filling state stored upon stopping the internal combustion engine is evaluated, i.e., it is established whether the fuel tank was, for example, greater than or equal to half full or less than or equal to half full.

If it is established that the fuel tank is greater than or equal to half full, then the stored correction signal is used until the new correction signal is established, since it is assumed that the tank has not been filled up after the internal combustion engine has been stopped, or if in fact fuel has been added, a falsification due to the additional fuel quantity is not serious.

If it is established that the fuel tank is less than half full, it is assumed that a filling operation has been conducted, and the last stored correction signal is corrected to an average correction signal (for example, that of a standard fuel) according to a predetermined function, for example, linear, exponential, stepped, etc. After establishing a new correction signal from the vaporization device, further operation is immediately corrected with the latter.

PROCESS COURSE B rapid tank filling indication

If it is established that there is no change in the tank filling state, the stored correction signal is used until a new correction signal is established.

If a change in the tank filling state is established, then process B continues as in the manner of process A in the state where it is established that the tank is less than half full.

For stoichimetric peration, it is possible to quantitatively check the correction signal and to adaptively adjust it in the case of a deviation.

In order to adapt the fuel quantity adhering to heating element 10 to the requirement with respect to measurement time and/or reproducibility of the sample quantity, a number of modifications in the surface state and the shape of heating element 10 may be of advantage.

Figure 3:
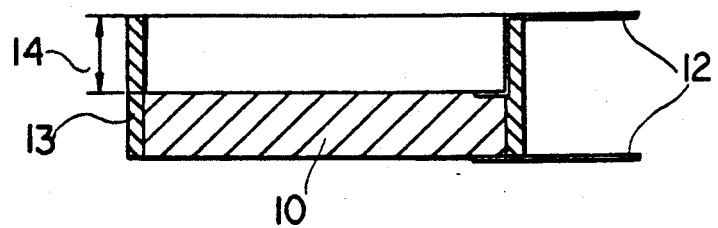
FIG. 3 is a sectional view through an embodiment of a PTC heating element.

FIG. 3 shows a heating element 10 formed as a PTC element, which is surrounded on its periphery with a casing 13, preferably of material with a small heat capacity and conductivity, which casing projects above the upper surface of PTC element 10 by a collar height 14 defining the fuel sample quantity If element 10 is, for example of, square cross-section, casing 13 will surround element at its sides and ends to define a cavity above the upper surface of the element 10 in which the fuel sample can be contained.

Figure 4:
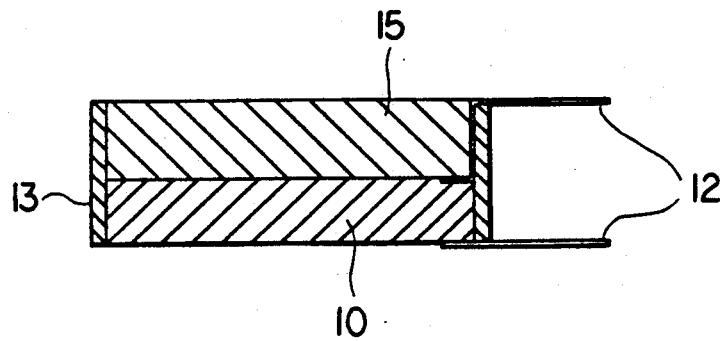
FIG. 4 is a sectional view through another embodiment of a PTC heating element.

In another embodiment of the PTC element according to FIG. 4, the cavity or space formed by collar height 14 is filled with a component 15, preferably made of porous material (e.g., sintered metal) to provide a certain insensitivity to position of the embodiment according to FIG. 3.

The PTC element can be provided on both sides with the component 15, and can be of any geometric form. The joining of the porous layers (sintered metal) with the PTC element can be effected by adhesives or soldering.

Figure 5:
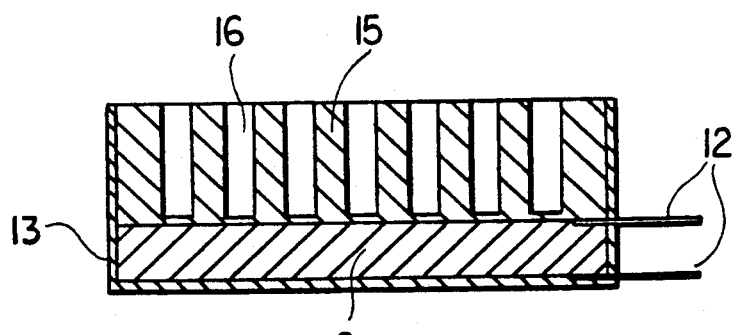
FIG. 5 is a sectional view through another embodiment of a PTC heating element.

In addition, component 15 may have recesses 16, as shown in FIG. 5, which may be in the shape of round holes, rectangular slots, polygon apertures or other geometric shapes. In this way, PTC element 10 can be completely encapsulated, if direct contact of the PTC element with the fuel should prove to be disadvantageous. The sealing of the PTC element 10 with respect to casing 13 and component 15 can be achieved by soldering or by an adhesive resistant to the fuel. The use of component 15 as a perforated plate makes possible a more rapid fuel exchange, if the latter should prove to be a problem for the porous material with respect to the capillary effect between the measurement processes.

Figure 6:
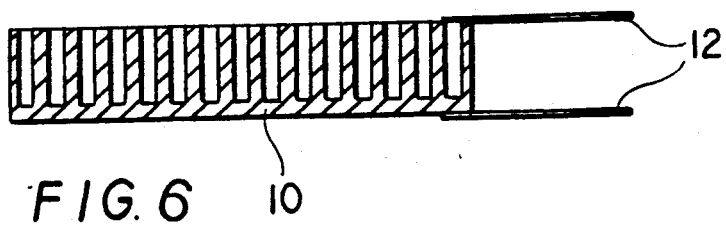
FIG. 6 is a sectional view through another embodiment of vaporization device.

For good compatibility of the material of the heating element with the fuel, heating element 10 may be constructed as a perforated plate as shown in FIG. 6, whose recesses 16 are designed as holes, but also may be slots, polygons, etc., the recesses being continuously open proceeding from their upper side, or are closed to the lower side. The PTC element 10 in the form of a perforated plate may also be produced from porous material.

In another embodiment of a device (not shown) for vaporization of a sample quantity of fuel, the device is preferably incorporated into the gas volume of the fuel tank and consists of a housing provided with inlet and outlet channels, in which the PTC element 10 is arranged and controlled by control lines 12. The outlet channel is opened and closed by means of a ⅜-way valve. In the periods between measurement, the housing with the PTC element is continuously filled with fuel, for example, by return of fuel by the mixture forming means to the tank, by means of a corresponding position of the ⅜-way valve. At the beginning of measurement, the ⅜-way valve is switched on by the electronic control device (not shown), whereby return fuel flows directly into the tank, bypassing the housing with the PTC element. At the same time, the voltage supply of the PTC is turned on, which heats the fuel sample present in the housing and a correction signal is formed according to the process described hereinbefore. After turning off the heating, ⅜-way valve is switched to "flood" the housing. After "flushing" the heated residual fuel sample from the housing, it is again ready for measurement.

Figure 7:
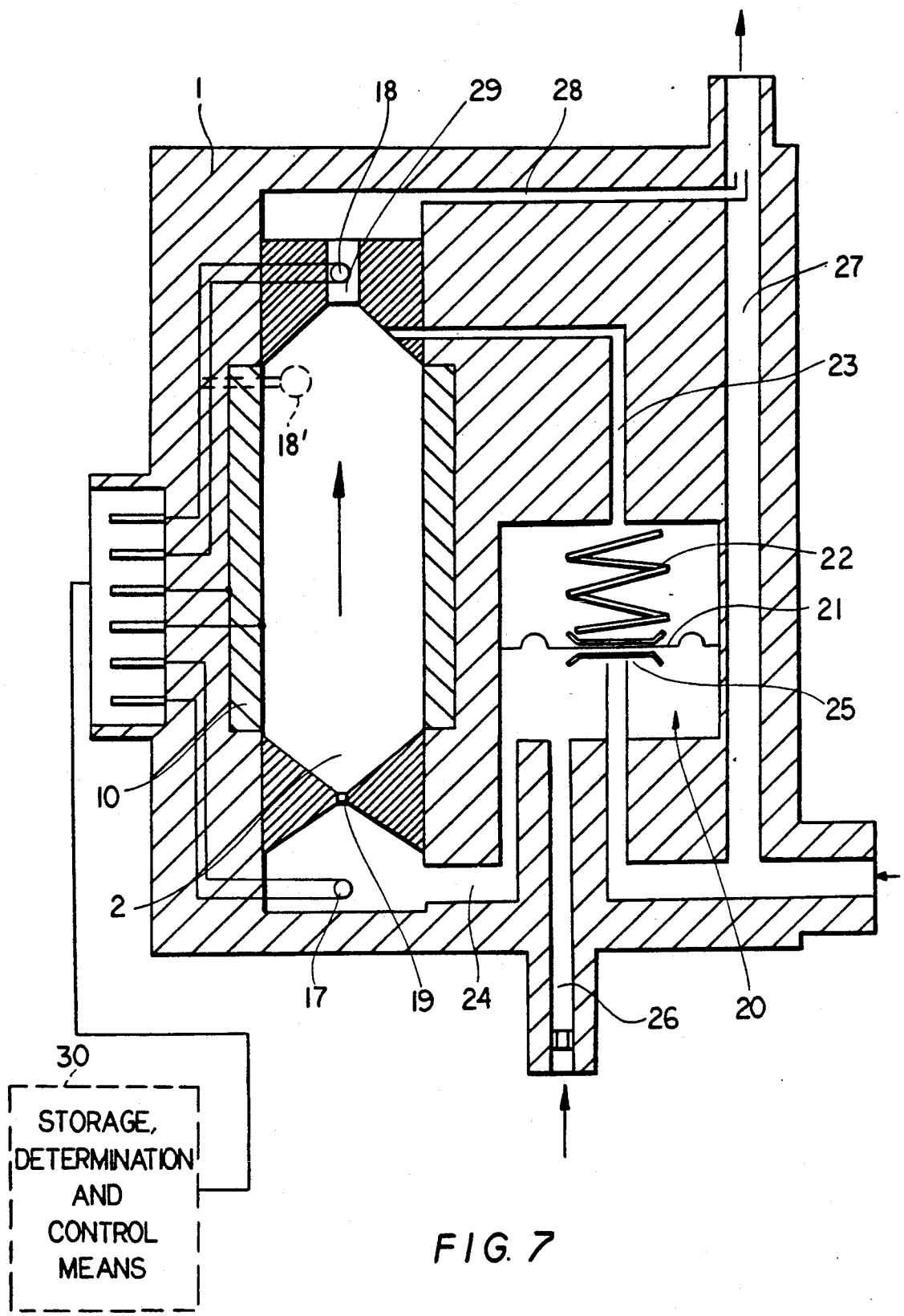
FIG. 7 is a section through another embodiment of vaporization device.

A device shown in FIG. 7 operates according to a somewhat different methodology, in which a continuous measurement and formation of the correction signal is possible.

The device according to FIG. 7 comprises housing 1 containing vaporization chamber 2 which can be heated by a tubular heating element composed as PTC element 10. The vaporization chamber 2 has an inlet channel 24, which is supplied with fuel from a supply channel 26 by means of a valve unit 20 constituted as a conventional differential pressure regulator, consisting of membrane 21, pressure spring 22 and valve 25, and an outlet channel 28, which opens into a return channel 27.

Vaporization chamber 2 incorporates respective temperature sensors 17, 18, a nozzle 19, and a measurement channel 29. Temperature sensor 17 is arranged, in the direction of flow, upstream of nozzle 19 and temperature sensor 18 is arranged in the center of measurement channel 29. In a modification the sensor 18 can be placed in proximity to PTC element 10 as shown at 18' in dotted outline in FIG. 7. 5 In a first process step, fuel is continuously delivered via nozzle 19 into vaporization chamber 2, and from the latter is transported through measurement channel 29 into return channel 27. In this way, the volume of fuel flow in vaporization chamber 2 is maintained constant by means of nozzle 19 and the differential pressure regulator 20, independent of the supply pressure in supply channel 26 and in return channel 27. The operation of differential pressure regulator 20 is well known in the art and requires no detailed description herein.

In the second process step, the vaporization chamber 2 is heated by means of PTC element 10, so that a temperature above the boiling point of an alcohol (e.g., 78° C. for ethanol) is produced in measurement channel 29 at temperature sensor 18, said temperature being continuously controlled by control of the heating capacity.

Distinctions between types of alcohol can be made by changing the set temperature at temperature sensor 18.

For fuel-alcohol mixtures, due to the temperature difference, an electrical output is produced deviating from the output produced by standard fuel (without alcohol) which is utilized to determine the type of alcohol and the content of alcohol in the fuel in a storage, determination and control means 30.

Thus, in a third process step, the magnitude of the controlled heating capacity is determined, and from this value a correction signal is formed by a comparison with a comparative value for standard fuel stored in a performance characteristic storage unit of the control device. In the fourth process step, as already described in the previous process, engine control values can be changed by means of the correction signal, and in the fifth process step, when the internal combustion engine is stopped, the last formed correction signal is stored until it is confirmed or replaced by a new signal based on a new fuel sample measurement.

In order to minimize the heat flow from heating element 10 or vaporization chamber 2 in housing 1, the housing is provided with heat insulation around the vaporization chamber.

In addition, vaporization chamber can be constructed so that an intensive heat transfer and mixing of the fuel sample is obtained. Thus, for example, the walls of the vaporization chamber may have surfaces of increasing curvature, or the vaporization chamber may be filled with fillers, or it may have a heat exchanger grid.

By special dimensioning of the insulation, the heat flow in the housing can be selected such that the latter indicates approximately the measurement in the region of the higher boiling point of ethanol, compared to that of methanol, as the product of the air requirement of methanol relative to the air requirement of ethanol times the vaporization heat of the methanol relative to the vaporization heat of ethanol.

With an intermittent measurement, after the determination of the measurement value, the voltage supply to heating element 10 is disconnected until the beginning of the next measurement.

Also in this process, the process steps already described above are applied with respect to the starting phase.

WHAT IS CLAIMED IS:

1. A process for detecting the concentration and type of alcohol in a fuel-alcohol fuel mixture, said process comprising heating a sample of a fuel mixture of fuel and alcohol to a temperature above the boiling point of the alcohol in said sample, measuring the temperature of said sample of fuel mixture during the heating of said fuel mixture, continuously correlating the measured temperature with respect to time to provide a measurement of temperature gradient with respect to time of the heated fuel mixture, detecting from said temperature gradient of said sample any interruption of increase of temperature during said heating, measuring the time interval during which temperature increase is interrupted, and determining the type of alcohol present in said fuel mixture and its concentration, from the value of the temperature at which the interruption of temperature increase takes place and the magnitude of the interval of time during which the temperature increase is interrupted.

2. A process as claimed in claim 1 to control operation of an internal combustion engine supplied with said fuel-alcohol fuel mixture, comprising producing a control signal based on the determination of the alcohol and its concentration in said fuel mixture and controlling the relative flow of air and said fuel mixture to an internal combustion engine based on said control signal so that the ratio of the air and the fuel mixture is substantially stoichiometric.

3. A process as claimed in claim 2 comprising effecting the heating and measuring of the fuel mixture to produce said control signal after starting the engine.

4. A process as claimed in claim 2 comprising detecting if fuel is added to a fuel tank for the engine and effecting said heating and measuring of the fuel mixture after the addition of fuel thereto.

5. A process as claimed in claim 1 comprising establishing a first temperature threshold below the boiling point of a selected alcohol, establishing a second temperature threshold above the boiling point of said selected alcohol, commencing the measurement of the time of interruption of said increase of temperature at said first threshold and terminating the measurement of said time of interruption at said second threshold.

6. A process as claimed in claim 1 comprising establishing at least one temperature threshold which is reached in less than a predetermined time period after commencement of measuring the interruption of temperature increase representative of vaporization time of the alcohol will initiate a new vaporization time measurement.

7. A process as claimed in claim 1 to control operation of an internal combustion engine supplied with said fuel-alcohol fuel mixture, comprising producing a control signal based on the determination of the alcohol and its concentration in said fuel mixture, using said control signal to regulate flow of air and fuel mixture to the engine and storing said signal for use to regulate flow of air and fuel mixture unless replaced by a subsequently produced control signal.

8. A process as claimed in claim 1 comprising initiating the measurement of interruption of temperature increase only when the rate of temperature increase, upon commencement of heating, is less than a predetermined value representative of the rate of temperature increase of said fuel alone.

9. A process as claimed in claim 1 comprising providing a vaporization chamber into which said sample is introduced and heated, injecting said fuel mixture into said vaporization chamber through a nozzle, discharging the fuel mixture from said vaporization chamber via a measurement channel and measuring the temperature of said fuel mixture in said measurement channel.

10. A process as claimed in claim 9 comprising maintaining the temperature measured in said measurement channel at a constant value related to the boiling point of a selected alcohol, by supplying heat to said vaporization chamber in an amount depending on the specific alcohol and its concentration in said fuel mixture, the variation in heat supplied to said vaporization chamber being representative of the specific alcohol and its concentration in said fuel mixture.

11. process as claimed in claim 10 comprising maintaining substantially constant pressure differential between the fuel mixture supplied to said nozzle and the fuel mixture discharged from the measurement channel.

12. A process as claimed in claim 1 comprising passing said fuel mixture at substantially constant flow through a heated vaporization chamber in which the temperature exceeds the boiling point of the alcohol in the fuel mixture, measuring the temperature of the fuel mixture after the latter has passed through the vaporization chamber, maintaining the heating of the fuel mixture in said vaporization chamber at a level to keep the temperature in the fuel mixture after passing through the vaporization chamber at a substantially constant value which is related to the boiling point of a selected alcohol, and measuring the heat supplied to the vaporization chamber which keeps the temperature of said fuel mixture at said substantially constant level to determine the specific alcohol and its concentration in said fuel mixture.

13. Apparatus for detecting the concentration and type of fuel-alcohol fuel mixture, said apparatus comprising:

a vaporization chamber, means for supplying a fuel mixture to said vaporization chamber, heating means for heating the fuel mixture in said vaporization chamber to a temperature above the boiling point of an alcohol component in the fuel mixture, means including temperature sensing means for determining the rate of change of temperature of said heated fuel mixture in said vaporization chamber with respect to time, the temperature increase of said fuel mixture during heating undergoing interruption at the boiling point of the particular alcohol present in said mixture due to the heat of vaporization of said particular alcohol, said interruption taking place over a time interval which is a function of the concentration of said particular alcohol in said mixture, and means for determining the particular alcohol and its concentration in said fuel mixture based on the difference between the heat of vaporization of different alcohols from one another and (b) the time interval during which said interruption in temperature increase takes place.

14. Apparatus as claimed in claim 13 comprising a housing in which said vaporization chamber is provided, inlet and outlet channels in said housing connected to said vaporization chamber, valve means for controlling flow of fuel mixture from the inlet channel to said vaporization chamber, said valve means comprising a displaceable valve body, spring means acting on said valve body, and actuator means acting on said valve body in opposition to said spring means to displace the valve body selectively between first and second positions, said valve body in one of said positions closing said inlet and outlet channels.

15. Apparatus as claimed in claim 14 wherein said housing has a return channel, said valve body in said one position opening said return channel whereas in said other position of the valve body, said inlet and outlet channels are open and said return channel is closed.

16. Apparatus as claimed in claim 15 wherein said temperature sensing means comprises a temperature sensor in said vaporization chamber in proximity to said heating means.

17. Apparatus as claimed in claim 15 wherein said heating means comprises a PTC element.

18. Apparatus as claimed in claim 17 comprising a casing for said PTC element which projects beyond said PTC element to define a space to retain a sample of the fuel mixture.

19. Apparatus as claimed in claim 18 comprising a component of porous material in said space.

20. Apparatus as claimed in claim 17 comprising a component on said PTC element for controlling the surface area of said PTC element exposed to the fuel sample.

21. Apparatus as claimed in claim 20 wherein said component is made of porous material.

22. Apparatus as claimed in claim 20 wherein said component has recesses.

23. Apparatus as claimed in claim 17 wherein said PTC element comprises a perforated plate having recesses disposed partly in the depth of the plate.

24. Apparatus as claimed in claim 13 wherein said vaporization chamber has an inlet with a nozzle thereat and an outlet with a measurement channel including a temperature sensor.

25. Apparatus as claimed in claim 24 comprising differential pressure valve means responsive to pressure in said inlet and outlet for maintaining a substantially constant supply of fuel mixture to said vaporization chamber.

* * * * *